Figure 1:
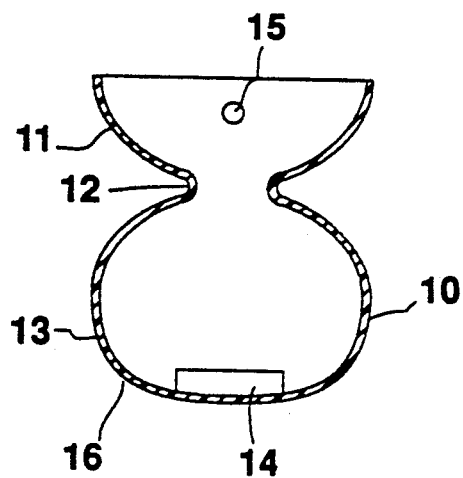

United States Patent [19]
Rosenberg

[11] Patent Number: 5,270,174
[45] Date of Patent: Dec. 14, 1993

[54] METHOD AND KIT FOR INDICATING THE LEVEL OF ORAL MICROBIAL ACTIVITY

[75] Inventor: Melvyn Rosenberg, Ramat-Gan, Israel

[73] Assignee: Assif Science and Technology Projects Development Ltd., Ramat-Gan, Israel

[21] Appl. No.: 329,876

[22] Filed: Mar. 28, 1989

Related U.S. Application Data

[63] Continuation-in-part of Ser. No. 174,669, Mar. 29, 1988, abandoned.

[30] Foreign Application Priority Data

Apr. 3, 1987 [IL] Israel ................................. 82095

[51] Int. Cl.⁵ ..................... C12Q 1/22; C12Q 1/04; C12Q 1/02
[52] U.S. Cl. ................................ 435/34; 435/26; 435/29; 435/30; 435/31; 435/32; 435/810; 436/1
[58] Field of Search .................... 435/26, 29, 32, 34, 435/810, 31, 30, 296, 287; 436/1, 64, 809; 424/71, 49; 422/102; 206/569, 520, 305; 248/152; 383/36

[56] References Cited

U.S. PATENT DOCUMENTS

| | | | |
|---|---|---|---|
| 3,797,734 | 3/1974 | Fleury et al. | 383/36 |
| 4,023,934 | 5/1974 | Spinner et al. | 422/86 |
| 4,208,187 | 6/1980 | Givner | 436/543 |
| 4,335,730 | 6/1982 | Griffin | 422/102 |
| 4,341,758 | 7/1982 | Sakakibara et al. | 436/533 |
| 4,397,944 | 8/1983 | Komura et al. | 435/34 |
| 4,528,269 | 7/1985 | Sandine et al. | 435/34 |
| 4,532,206 | 7/1985 | Robinson et al. | 435/34 |
| 4,582,795 | 4/1986 | Shibuya et al. | 435/34 |
| 4,589,548 | 5/1986 | Fay | 206/569 |
| 4,591,554 | 5/1986 | Koumura et al. | 435/34 |
| 4,618,691 | 10/1986 | Medina et al. | 435/227 |
| 4,761,379 | 8/1988 | Williams et al. | 435/810 |
| 4,775,626 | 10/1988 | Armenta | 435/244 |

FOREIGN PATENT DOCUMENTS

| | | | |
|---|---|---|---|
| 0234443 | 4/1986 | Fed. Rep. of Germany | 435/34 |
| 50-38717 | 12/1975 | Japan | 435/34 |
| 1165989 | 7/1985 | U.S.S.R. | 436/164 |

OTHER PUBLICATIONS

Mustakallio, "Tetrazolium Reduction Test for Milk", Nov. 1955, Science, pp. 971-972.
Webster's New World Dictionary of the American Language, 1968 p. 1475.
Colowick et al, Methods of Enzymology 1957, vol. IV, pp. 330-331.

*Primary Examiner*—Toni R. Scheiner
*Attorney, Agent, or Firm*—Benjamin J. Barish

[57] ABSTRACT

The invention provides a method for indicating the level of oral microbial activity comprising providing a sterile liquid for introduction into the oral cavity for swishing therein, providing a transparent vessel having therein an indicator which undergoes a characteristic color change in the presence of oxygen-consuming microbes and placing the swished liquid together with nutrients to enhance microbial growth in the vessel, whereby the indicator undergoes a color change as a function of time, which color change is an indication of the level of microbial activity in the swished expectorated liquid. The invention also provides a kit for use in carrying out the method comprising a sterile liquid, a transparent vessel for use in receiving the expectorate, and an indicator to be provided in the vessel to produce a visual indication of the level of microbial activity in the expectorated liquid.

7 Claims, 1 Drawing Sheet

METHOD AND KIT FOR INDICATING THE LEVEL OF ORAL MICROBIAL ACTIVITY

The present specification is a continuation-in-part of U.S. Ser. No. 07/174,669 filed Mar. 29, 1988, now abandoned.

The present invention relates to a method and kit to ascertain and measure the level of the microbial activity and concomitant clinical parameters in the mouth, by either dental practitioners, or auxiliary staff or by patients themselves.

Many oral ailments (bad breath, caries and periodontal diseases) can be related to microbial activity ill the mouth. Bad breath (halitosis) is usually related to oral accumulation of microorganisms, e.g., subgingival dental plaque, between the teeth, under a prosthesis, on the tongue, etc.

Thus as reported in the literature, increased levels of dental plaque results in dental caries and/or periodontal disease. Whereas dental caries is commonly associated with elevated levels of Streptococcus mutans (Loescne, W. J. 1986. Role of Streptococcus mutans in human dental decay. Microbiol. Rev. 50:353-380), periodontal disease is accompanied by elevated levels of more than 57 bacterial species (Moore, W. E. DC., L. V. Holdeman, E. P. Cato, R. M. Smibert, J. A. Burmaister, K. G. Palcanis and R. R. Ranney. 1985. Comparative bacteriology of juvenile periodontitis. Infect. Immun. 48:507-519).

Similarly, halitosis (bad breath) is related to the metabolism of a variety of microorganisms which produce hydrogen sulphide, mercaptans, and other cytotoxic, putrid volatile gases, generally under anaerobic conditions (Tonzetich, J. 1977. Production and origin of oral malador: a review of mechanisms and methods of analysis. J. Periodontol. 48:13-20).

There is little, if any, doubt today that chronic inflammatory periodontal disease results from bacterial plaque accumulation as can be learned, e.g., from Slots J. 1979. Sublingual microflora and periodontal disease. J. Clin. Periodontol. 8:351 and Hiederman van Palenstein, W. H. 1981. Microbial aetiology of periodontal disease. J. Clin. Periodontol. 8:261.

Since as reported, e.g. by Schluger, S., A. Yuodelis and R. Page. 1979 Epidemiology of periodontal disease, pp. 23-87 In Periodontal Disease (1st ed.), Lea & Febiger, Philadelphia, Pa., periodontal disease in its different forms affects most of the world's population, much attention has been given to diagnostic means: bleeding indices, plaque and periodontal indices, clinical probing, etc. Most available techniques require sophisticated skills, and costly doctor's "chair" time. Simple methods which may be carried out by office auxilliaries, yet providing reliable and valid data, are therefore essential.

It is of great benefit to the dental practitioner and to the patient to have at their disposal criteria with which to measure the oral levels of bacteria or other microorganisms (e.g., yeast). Some methods enable assessment of specific organisms in the mouth, such as plating of saliva samples on selective growth media, for estimation of lactobacilli, Streptococcus mutans or yeast. However, these methods do not provide an overall picture of oral microbial activity, and give results only after several days. One rapid test is to estimate the level of bacterial accumulation on the tooth surfaces (supergingival dental plaque), using a dye such as erythrosine, but this test does not provide an overall picture of the microbial activity in the mouth.

An object of the present invention is to provide a simple and convenient method for the measurement of the overall level of oral hygiene, which can be correlated to oral ailments, e.g., bad breath and periodontal disease.

Another object of the invention is to provide a kit for use in practicing the above method.

According to the present invention, there is provided a method for indicating the level of oral microbial activity comprising:

providing a sterile liquid for introduction into the oral cavity for swishing therein, providing a transparent vessel having therein an indicator which undergoes a characteristic color change in the presence of oxygen-consuming microbes and placing said swished liquid together with nutrients to enhance microbial growth in said vessel, whereby said indicator undergoes a color change as a function of time, which color change is an indication of the level of microbial activity in said swished expectorated liquid.

In preferred embodiments of the present invention said sterile liquid is one which contains nutrients to enhance microbial growth and also has good cleansing properties and is preferably selected from sterilized milk, a milk-based liquid or a conventional milk substitute.

Alternatively, said sterile liquid is water and said vessel is provided with an indicator which undergoes a characteristic color change in the presence of oxygen-consuming microbes and with a nutrient containing substance to enhance microbial growth.

According to a further feature of the invention, there is provided a kit comprising a sterile liquid, a transparent vessel for use in receiving the expectorate, and an indicator to be provided in the vessel and to produce a visual indication of the level of microbial activity in the expectorated liquid; the kit preferably also includes a color chart indicating the various levels of microbial activity present when a predetermined color change is produced over a predetermined time interval in all the material in the vessel, or at calibrated levels in the vessel. The color chart can be used to indicate the level of microbial activity by measuring the color change after a predetermined time interval, or by measuring the time interval for a predetermined color change to take place.

According to another feature of the invention there is provided a preferred kit for use in indicating the level of oral microbial activity in accordance with the method herein defined, comprising a sterile liquid having cleansing properties and containing nutrients to enhance microbial growth, a transparent vessel for use in receiving the expectorate, an indicator to be provided in the vessel to produce a visual indication of the level of microbial activity in the expectorated liquid and a stand for receiving and holding said vessel, said stand comprising a supported elevated platform provided with an aperture sized to receive the bottom of said vessel, and a mirrored surface provided directly below said aperture through which mirrored surface the color change in the bottom of said vessel protruding downwardly through said aperture can be indirectly viewed.

Further features and advantages of the invention will be apparent from the description below.

The invention is herein described by way of example only, with reference to the examples set forth below, and also with reference to the accompanying drawings, wherein:

FIG. 1 pictorially illustrates a vessel which may be included in a kit to be used for practicing the method of the present invention.

Figure 2:
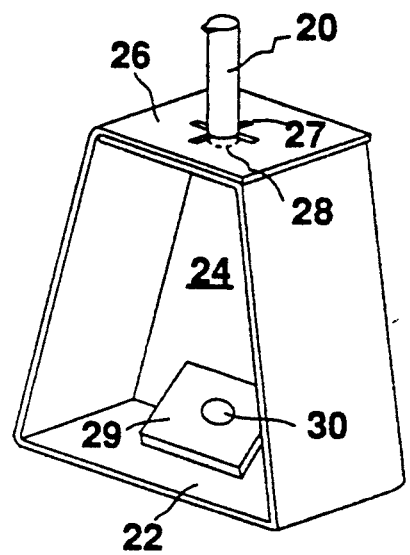
Figure 3:
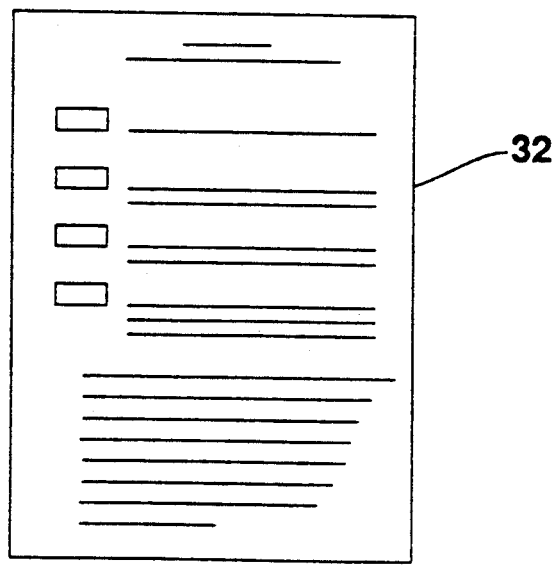

FIG. 2 pictorially illustrates components of an especially preferred kit to be used for practicing the method of the present invention, and FIG. 3 pictorially illustrates a color chart that may also be included in the kit.

As described above, the microbial sample is obtained from the oral cavity by swishing with a liquid. The liquid should have several properties, including the following: (i) it should be sterile prior to its introduction into the oral cavity; (ii) it should have good cleansing properties; (iii) it should not harm the microbial population; and (iv) it should provide nutrients and physiological conditions conducive to microbial activities. Among the liquids tested, sterilized milk has proven a suitable liquid for this purpose. There may also be used other milk-based liquids or milk substitutes.

The liquid may also include a selective agent to indicate certain populations of microbial activity. For example, the liquid could include chloramphenicol, to indicate yeast activity.

A given volume of the sterile liquid (e.g. 10 ml) is introduced into the oral cavity, and the patient is asked to swish vigorously for e.g., 30 seconds. The liquid is then expectorated into a vessel.

FIG. 1 pictorially illustrates one form of vessel that may be used. The vessel 10 comprises a large-diameter upper funnel section so that expectoration is conveniently accomplished. If the microbial activity is to be assessed by oxygen consumption, the funnel section 11 leads, via a small diameter bore 12 through which the liquid can percolate, into a lower compartment 13. The lower compartment contains, either in liquid or solid form, an indicator 14 of microbial activity. The lower compartment may also contain additional nutrients, such as Brain Heart Infusion Broth or glucose. In the examples given below, the indicator consists of methylene blue, which turns from blue to colorless upon reduction, e.g. exhaustion of oxygen. Other possible indications such as $H_2S$ (hydrogen sulphide) detection, or pH changes, or combinations thereof, could also be used for measuring the level of microbial activity.

As opposed to the conventional cuspidors designed to conceal expectorates, the vessel 10 described here should be transparent, in order to enable visualization of the color changes. It is preferably made of an insulating material, e.g., a plastic such as polystyrene, so that the temperature of ca. 35° C. degrees attained during the swishing procedure is conserved. Ideally, the upper section 11 should be funnel-shaped since the expectorated microorganisms are often aggregated, or adhering to epithelial cells or debris and these should be allowed to fall freely to the bottom 13 of the vessel in order to expedite the results. Vessel 10 may also have a hole 15 in its top section 11 permitting the vessel to be hung on the wall. Its bottom 16 should be flat to permit it to stably rest on a flat horizontal surface, or the vessel could be provided with legs (not shown) for this purpose or placed in a stand.

Alternatively, and preferably as shown in FIG. 2 the vessel is in the form of a test tube 20 and the kit contains a stand 22 supporting by means of an upright member 24, which can be a rod or wall of a container, an elevated platform 26. The platform is provided with an aperture 27 sized to receive the bottom 28 of said test tube 20 which protrudes downwardly therethrough. A tilted mirrored surface 29 is provided directly below said aperture 27 in which the reflection 30 of said downwardly protruding bottom portion 28 can be seen so that the color change in the bottom of the test tube can be readily indirectly viewed through said mirror 29.

A timer may be used to indicate the time required for testing the color change of the liquid. In addition, to facilitate the measurement of microbial activity in the liquid, and hence determine the level of microbial activity indicated by the color change of the liquid, a color chart, shown as 32 in FIG. 3, is provided to show the different levels of microbial activity. The user may compare, at the end of the incubation period, the color of the liquid at the bottom of the vessel, with the color chart, and thereby read the microbial activity level.

The sterilization process of the liquid can be done by irradiation, ultra-high temperatures, autoclave and such process known per se for this purpose.

EXAMPLE 1

A patient was asked to swish in his mouth, for 30 seconds, a 10 milliliter sample of ultra-high temperature (UHT) sterilized commercial cow's milk, 3% butterfat (Tnuva, Rehovot). The expectorate was collected in a transparent plastic vessel. The expectorate was then serially diluted with sterile milk. To 3 ml of the dilutions, 0.1 ml of a 0.1% aqueous solution of methylene blue were added, and following mixing, allowed to stand at 37° C. The time required for the milk at the very bottom of the test tube to turn from blue (aerobic) to white (anaerobic) was recorded. The results are recorded in the following table:

TABLE 1

| Dilution | White after |
| --- | --- |
| Undiluted expectorate | 10 minutes |
| 1:4 | 70 minutes |
| 1:16 | 240 minutes |
| 1:32 | 360 minutes |

This data shows that the time required for the bottom of the sample to turn white increases with decreasing numbers of the microorganisms in the sample.

EXAMPLE 2

A volunteer with poor oral hygiene and bad breath swished 10 ml milk in his mouth as in the previous experiment. The milk was expectorated, mixed immediately with 0.4 ml of methylene blue solution (0.1%), and incubated at room temperature in a transparent plastic vessel. The volunteer then brushed his teeth and was asked to repeat the swishing experiment. Whereas the bulk of the prebrushing suspension turned white after 30 minutes incubation, the suspension following brushing turned white after 65 minutes.

In contrast, the suspension of a volunteer with excellent oral hygiene, obtained at the same time and under the same conditions as that of the volunteer with poor oral hygiene, did not turn appreciably white following 100 minutes incubation.

EXAMPLE 3

The following example shows the correlation between bacterial level in the milk in twenty-nine adult volunteers:

The twenty-nine adult volunteers each swished 10 ml UHT sterilized 3% milk in their mouths for thirty seconds as in the previous experiment. In each instance, the milk was expectorated, and a sample taken for bacterial counts (colony forming units on Brain Heart Infusion Agar, following two days aerobic incubation at 37° C.). 3 ml of the expectorated sample was immediately transferred into a test tube containing 0.12 ml of a 0.1% aqueous solution of methylene blue. Following several seconds mixing, the test tubes were stoppered and allowed to stand. The time required for the milk within a predetermined volume at the bottom of the test tube to turn from blue to white was recorded. The results, summarized below, clearly show that the duration of the color change is inversely related to the microbial count. For example, nine of eleven samples with more than 20,000,000 cfu/ml exhibited a color change within one hour; eleven of twelve samples with less than 10,000,000 cfu/ml exhibited a color change following more than an hour. When the logarithm of the microbial count is plotted against the logarithm of the duration, a high significant correlation (probability <0.001) is obtained, with a correlation coefficient (r) value of −0.849.

TABLE 2

Distribution of Results:

| Number of samples yielding | Time required for color change | |
|---|---|---|
| | Less than 60 min. | More than 60 min. |
| 0-10,000,000 cfu/ml | 1 | 11 |
| 10,000,000-20,000,000 cfu/ml | 4 | 2 |
| more than 20,000,000 cfu/ml | 9 | 2 |

As can be seen from the above table the number of samples with rapid color change (less than 60 min) increases as the number of microbes goes up. Conversely, the number of samples turning white after more than one hour increases as the number of microbes goes down.

Statistical analysis of the data reveal that there is a highly significant correlation between the decrease in the time required for the color change (indicative of a high rate of oxygen consumption) and the increase in number of microorganisms in the sample.

EXAMPLE 4

One important aspect of the test is its potential correlation with clinical parameters. A study was performed with 49 volunteers attending a private periodontal clinic. Forty-three of the volunteers were graded according to the presence of moderate or severe periodontal disease (as opposed to no periodontal disease).

Forty-nine patients in a private periodontal practice participated in the study. These patients received periodontal treatment at different stages, i.e. before periodontal examination, prior to or during initial therapy, after initial therapy, and following periodontal surgery. The age and sex of each patient were available. In addition, the last time prior to the milk test at which patients ate or drank was recorded. The periodontal status of each patient was determined according to the *Gingival Index* and *Periodontal Index*, Russell, A. L. 1956, A system of classification and scoring for prevalence surveys of periodontal disease, J. Dent. Res. 35:350, and the plaque level was scored using the *Turesky Plaque Index*, Turesky, S., N. Gilmore and I. Glickman, 1970. Reduced plaque formation by chlormethyl analogue of vitamin C. J. Periodontol. 41:41, on a scale of 0-4.

Each patient swished his mouth for 30 sec with 10 ml of sterile, ultra high temperature sterilized 3% milk (Tnuva, Rehovot) provided with the kit of FIG. 2. The expectorate was collected into a small cup; 3 ml of the expectorate were immediately removed into a disposable test tube (Costar, 10 mm diameter, 12 mm length), containing 0.12 ml of methylene blue (0.1% aqueous solution). The test tube was capped, mixed briefly, placed in an aperture 27 having a diameter of 6 mm of platform 26 of stand 22 and allowed to stand over a tilted mirror 29. The time required for a color change (blue-to-white) within a 6 mm diameter circle drawn on the bottom of the tube was recorded. The correlation between Plaque Index levels and the logarithm of time required for the color change were calculated by linear regression analysis; similar correlations were established for age of the patient and milk test results. The correlations between periodontal status and milk test results were analyzed using the t-test for sample populations.

The relationship between the time required for color change, and plaque index and the statistical relationships between the time required for color change, and other parameters, is summarized in Table 3. When all 49 patients were considered together, linear regression analysis of the logarithm of time required for color change as function of Plaque Index yielded a correlation coefficient of −0.579 ($p<0.001$). However, when the nineteen patients who ate or drank within 90 minutes prior to the test were excluded, the correlation coefficient increased to −0.641 ($p<0.001$); the correlation coefficient of only those who ate or drank within 90 minutes of the test was −0.481 ($p<0.05$).

TABLE 3

Statistical Data Summary
1. Linear Regression Analysis

| Population | Parameter | number (n) | correlation coefficient (r) | p< |
|---|---|---|---|---|
| Patients checked | Plaque index | 49 | −0.579 | 0.001 |
| Excluding those who ate or drank prior to test | P.I. | 30 | −0.641 | 0.001 |
| Only those who ate or drank prior to test | | 19 | −0.481 | 0.05 |
| Patients | Age | 49 | −0.337 | 0.02 |

TABLE 4

| Group | No. of volunteers | Average Time for Color Change (min) |
|---|---|---|
| No periodontal disease | 30 | 227 |
| Moderate periodontal disease | 8 | 96 |
| Severe periodontal disease | 5 | 79 |
| Not assessed | 6 | — |

Among 43 patients who were scored for periodontal disease status (five were not scored), 8 were recorded as having moderate gingivitis and 5 as severe gingivitis. Whereas the means time for the color change was 227 min for the control (no periodontal disease) group (n=30), the mean times for the moderate (n=8) and severe (n=5) groups were only 96 and 79 min, respectively. Despite the small numbers of patients with diseased states, both moderate and severe gingivitis groups differed significantly as compared to the control group. The significance level was less for severe vs. control ($p<0.05$) than for moderate vs. control ($p<0.025$), probably due to the smaller number of patients in the severe category.

CONCLUSIONS

1. The test proved to be simple and rapid, requiring no special skills.
2. High correlations with clinical parameters (Plaque Index and periodontal status) were found.
3. The test was liked by the patients who were impressed by the proficiency level of treatment.

Statistical evaluation showed that both moderate and severe periodontal disease groups differed significantly as compared to the control group.

EXAMPLE 5

A volunteer swished his mouth as described in Example 1. The expectorate was diluted serially using sterile milk (prewarmed to 37 degrees Celsius). To test tubes containing 0.12 ml of a 0.1% aqueous solution of methylene blue were added 3 ml of expectorate (or dilution thereof). The test tubes, containing the original expectorate and various dilutions, were allowed to stand at room temperature. The times required for color change (blue-to-white) within 6 mm diameter at the bottom of each test tube were recorded. Microbiological counts (colony forming units) were determined. The correlation between the time required for the color change and the microbial levels in the dilutions are shown below:

TABLE 5

| Millions of colony forming units/ml | Time for color change (min) |
| --- | --- |
| 30 | 6 |
| 21 | 16 |
| 15 | 22 |
| 6 | 60 |
| 3 | 120 |
| 0.21 | 290 |

If one plots the logarithm of the number of microorganisms in the sample as a function of the logarithm of the time required for the color change, a straight line is obtained. Statistical evaluation yields an extremely significant correlation between the microbial level in the sample and the time required for the color change at the bottom of the test tube.

EXAMPLE 6

One commonly used method for improving oral hygiene at home is use of an active mouthwash preparation. Two experiments were performed in order to see whether use of such a preparation resulted in concomitant changes in the results of the test. Volunteers were asked to swish for two consecutive 15 second periods with either a potent commercial mouthwash (Listermint, Warner and Lambert, Eastleigh, Hampshire, U.K.) as opposed to a placebo mouthwash (i.e. no active ingredients) (Agis Ltd., 26 Marmorek Street, Tel Aviv, Israel). Prior to the swishing and 30 minutes following swishing, volunteers performed the test as described in the previous example. The results are presented below:

TABLE 6

| Volunteer Number | Time required for color change (minutes) | | | |
| --- | --- | --- | --- | --- |
| | MOUTHWASH | | PLACEBO | |
| | before | after | before | after |
| 1 | 39 | 1010 | — | — |
| 2 | 76 | 530 | — | — |
| 3 | 44 | 312 | — | — |
| 4 | 18 | 449 | — | — |
| 5 | 76 | 338 | — | — |
| 6 | — | — | 60 | 118 |
| 7 | — | — | 99 | 76 |
| 8 | — | — | 44 | 89 |
| 9 | — | — | 96 | 82 |
| 10 | — | — | 13 | 59 |
| 11 | — | — | 32 | 54 |

As can be seen from the results, in each case swishing with the active mouthwash brought about a large increase in the time required for the color change, as opposed to before using the mouthwash. On the average, the time required increased by a factor of 13.9 in the mouthwash group. On the other hand, the group usng the placebo showed a small increase, by a factor of only 2.03 on the average. Statistical analysis shows that these are highly significant differences, and thus shows that the test correlates with a clinical procedure.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for indicating the level of oral microbial activity, comprising the steps of:
    (a) providing a sterile liquid containing nutrients to enhance microbial growth, for introduction into the oral cavity for rinsing therein, said sterile liquid being selected from the group consisting of milk, a milk-based liquid and a milk substitute;
    (b) providing a transparent vessel having therein an indicator which undergoes a characteristic color change upon exhaustion of oxygen, in the presence of oxygen-consuming microbes;
    (c) having a patient rinse his or her oral cavity with said sterile liquid and then expectorate the resultant rinse liquid; and
    (d) placing said expectorated rinse liquid in said vessel,
whereby said indicator undergoes a color change as a function of time, which color change is an indication of the level of microbial activity in said expectorated rinse liquid.

2. The method according to claim 1, wherein the indicator is methylene blue which turns from blue to white upon the consumption of oxygen by the microbes within the expectorated liquid.

3. A kit for use in indicating the level of oral microbial activity, comprising:
    a sterile liquid selected from the group consisting of milk, a milk-based liquid, and a milk-substitute;

a transparent vessel for use in receiving an expectorate which consists essentially of the resultant liquid obtained by rinsing a patient's oral cavity with said sterile liquid and expectorating the liquid and entrained oxygen-consuming microbes;

an indicator which undergoes a characteristic color change upon exhaustion of oxygen, in the presence of oxygen-consuming microbes, to be provided in the vessel to produce a visual indication of the level of microbial activity in the expectorated liquid;

and a color chart indicating the various levels of microbial activity present when a predetermined color change is produced over a predetermined time interval.

4. A kit according to claim 3 wherein said vessel is of transparent material and includes an upper funnel section for receiving the expectorate, said funnel section communicating with a lower compartment containing the indicator and in which the test is performed.

5. A kit according to claim 3 wherein said vessel is of polystyrene.

6. A kit according to claim 3, wherein the vessel includes calibration markings defining a volume at the bottom of said vessel in which the level of microbial activity of the expectorate contained in said defined volume can be determined by measuring the time required for a predetermined color change to appear in said defined volume.

7. A kit for use in indicating the level of oral microbial activity according to claim 3 wherein said vessel is a test tube and further comprising a stand for receiving and holding said vessel, said stand comprising a supported elevated platform provided with an aperture sized to receive the bottom of said vessel, and a mirrored surface provided below said aperture through which mirrored surface the color change in the bottom of said vessel can be indirectly viewed.

* * * * *